(12) United States Patent
Mewshaw et al.

(10) Patent No.: US 6,337,336 B1
(45) Date of Patent: Jan. 8, 2002

(54) AZAINDOLE DERIVATIVES FOR THE TREATMENT OF DEPRESSION

(75) Inventors: Richard E. Mewshaw, King of Prussia, PA (US); Kristin L. Meagher, Hightstown, NJ (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/551,134

(22) Filed: Apr. 17, 2000

Related U.S. Application Data

(60) Provisional application No. 60/219,530, filed on Apr. 22, 1999.

(51) Int. Cl.[7] ............... A61K 31/44; C07D 471/02; C07D 491/02; C07D 498/02; C07D 513/02
(52) U.S. Cl. ............................ 514/300; 546/113
(58) Field of Search ..................... 514/300; 546/113

(56) References Cited

U.S. PATENT DOCUMENTS 5,627,196 A    5/1997    Audia et al.

FOREIGN PATENT DOCUMENTS

WO    0714894    11/1995

OTHER PUBLICATIONS

Le Poul et al; Early desensitization of somato–dendritic 5–ht1 autoreceptors in rats treated with fluoxetine or paroxetine; Arch Pharmacol (1995) 352: 141–148.

Artigas et al; Acceleration of the effect of selected antidepressant drugs in major depression by 5 Ht1a antagonists; Trends Neurosci, (1996) 19, 378–383.

Malleron et al; New Indole Derivatives as Potent and Selective Serotonin Uptake Inhibitors; J. Med. Chem. 1993, 36, 1194–1202.

*Primary Examiner*—Frederick Krass

(57) ABSTRACT

Compounds useful in the treatment of diseases affected by disorders of the serotonin-affected neurological systems, such as depression and anxiety, are provided having the following formula:

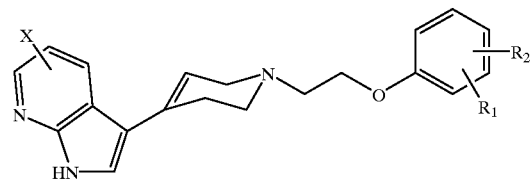

wherein:

$R_1$ and $R_2$ form a carbocyclic ring of 5 to 7 carbon atoms, wherein said ring may be saturated or unsaturated and may contain one or more heteroatoms; and X is independently hydrogen, cyano, carbamoyl, halogen or alkoxy; or pharmaceutically acceptable salts thereof.

7 Claims, No Drawings

AZAINDOLE DERIVATIVES FOR THE TREATMENT OF DEPRESSION

CROSS REFERENCE TO RELATED APPLICATIONS

This application claims the benefit of U.S. Provisional Application No. 60/219,530, filed Apr. 22, 1999, which was converted from U.S. application Ser. No. 09/296,736, filed Apr. 22, 1999, now abandoned.

FIELD OF INVENTION

This invention relates to compounds useful for the treatment of diseases affected by disorders of the serotonin-affected neurological systems, such as depression and anxiety. More specifically, the present invention is directed to aryl piperazinyl cyclohexyl derivatives useful for the treatment of such disorders.

BACKGROUND OF INVENTION

Pharmaceuticals which enhance the neurotransmission of serotonin (5-HT) are useful for the treatment of many psychiatric disorders, including depression and anxiety. The first generation of non-selective serotonin-affecting drugs operated through a variety of physiological means which caused them to possess numerous undesired side-effects. The more recently prescribed drugs, the selective serotonin reuptake inhibitors (SSRIs), act predominately by inhibiting 5-HT, which is released at the synapses, from being actively removed from the synaptic cleft via a presynaptic serotonin transport carrier. Since SSRIs require several weeks before they exert their full therapeutic effect, this 5-HT blockade mechanism cannot fully account for their therapeutic activity. It is speculated that this two week induction which occurs before a full antidepressant effect is observed, is due to the involvement of the 5-HT1A autoreceptors which suppress the firing activity of 5-HT neurons, causing a dampening of the therapeutic effect. Studies suggest that after several weeks of SSRI administration, a desensitization of the 5-HT autoreceptors occurs allowing a full antidepressant effect in most patients. (See, e.g., Le Poul et al., *Arch. Pharmacol.*, 352:141 (1995)). Hence, it is believed that overriding this negative feedback by using 5HT1A antagonists would potentially increase and accelerate the clinical antidepressant response. Recent studies by Artigas et al., *Trends Neurosci.*, 19:378–383 (1996), suggest a combination of 5-HT1A activity and inhibition of 5-HT uptake within a single molecular entity can achieve a more robust and fast-acting antidepressant effect.

European Patent Application No. 0714894A1 discloses the preparation of the following compounds as 5HT1A agonists for the treatment of migraine headaches.

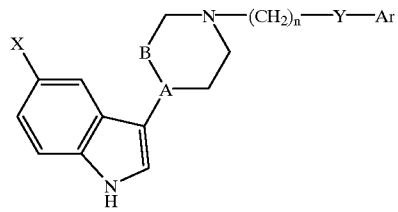

wherein:

A—B is —CH—CH, or —C=CH—;

X is H, halo, $C_1$–$C_4$ alkoxy, $C_1$–$C_4$ alkylthio, $C_1$–$C_4$ alkyl, benzyloxy, hydroxy or carbaxamido;

Y is O, S or a bond;

n is 1–4; and

Ar is 1-naphthyl, 2-naphthyl, phenyl or phenyl, mono-substituted with a substituent selected from the group consisting of halo, $C_{1-4}$ alkoxy, $C_{1-4}$ alkylthio, $C_{1-4}$ benzyloxy hydroxy or trifluoromethyl.

U.S. Pat. No. 5,627,196 discloses compounds of the following formula as having effects on serotonin-related systems.

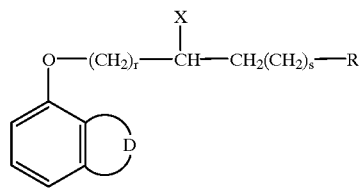

wherein r is 0–4;

s is 0–1; and

D is a residue which combines with the carbon atoms to which it is attached to complete a pyrrolyl, irnidazolyl, pyridinyl, pyrazinyl, pyridazinyl or pyrimidinyl group;

X is hydrogen, phenyl, hydroxy or methoxy provided that X is hydrogen or phenyl where r is 0; and R is —NH—$R_1$,

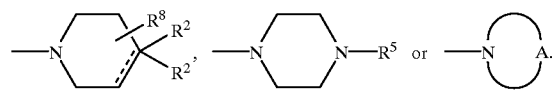

Malleron et al., *J. Med. Chem.* 36:1194–1202 (1983)) discloses indole derivatives as serotonin uptake inhibitors having the basic formula:

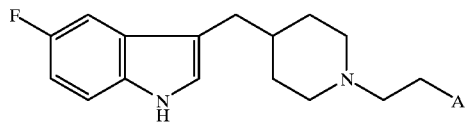

wherein A may be:

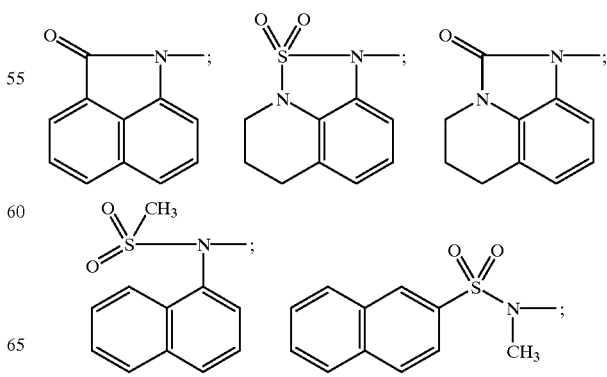

-continued

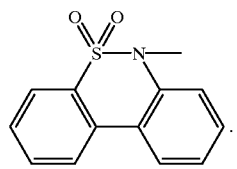

SUMMARY OF INVENTION

The compounds of this invention are aryloxy piperidinyl indoles represented by Formula I:

I wherein:
R$_1$ and R$_2$ form a carbocyclic ring of 5 to 7 carbon atoms, wherein said ring may be saturated or unsaturated and may contain one or more heroatoms; and
X is independently hydrogen, cyano, carbamoyl, halogen or alkoxy; or pharmaceutically acceptable salts thereof.

DETAILED DESCRIPTION OF THE INVENTION

The compounds of the present invention are preferably those of Formla I, wherein:
R$_1$ and R$_2$ form a carbocyclic ring of 5–6 carbon atoms, containing one or more heteroatoms; and X is hydrogen; or pharmaceutically acceptable salts thereof.

Most preferably, the compounds of the present invention are selected from the following:

3-{1-[2-(2,3-Dihydro-benzo[1,4]dioxin-5-yloxy)-ethyl]-1,2,3,6-tetrahydro-pyridin-4-yl}-1H-pyrrolo[2,3-b]pyridine;
3-{1-[2-(1H-Indol-4-yloxy)-ethyl]-1,2,3,6-tetrahydro-pyridin-4-yl}-1H-pyrrolo[2,3-b]pyridine; and
5-{2-[4-(1H-Pyrrolo[2,3-b]-pyridine-3-yl)-3,6-dihydro-2H-pyridin-1-yl]-ethoxy}-quinoline.

As used herein, the term "alkoxy" is meant to include both straight and branched carbon chains containing 1–6 carbon atoms. The term "halogen" is meant to include fluorine, chlorine, bromine and iodine. The term "heteroatom" is meant to include oxygen, nitrogen and sulfur.

The compounds of Formula I also may be used in the form of a pharmaceutically acceptable acid addition salt having the utility of the free base. Such salts, prepared by methods well known to the art are formed with both inorganic or organic acids, for example: fumaric, maleic, benzoic, ascorbic, pamoic, succinic, bismethylenesalicylic, methanesulfonic, ethanedisulfonic, acetic, oxalic, propionic, tartaric, salicyclic, citric, gluconic, lactic, malic, mandelic, cinnamic, citraconic, aspartic, stearic, palmitic, itaconic, glycolic, p-aminobenzoic, glutamic, benzene-sulfonic, hydrochloric hydrobromic, sulfuric, cyclohexylsulfaric, phosphoric and nitric acids.

The compounds of the present invention may be prepared by any suitable method which will be recognized by those skilled in the art. However, the present compounds may be advantageously prepared according to Scheme 1 set forth below.

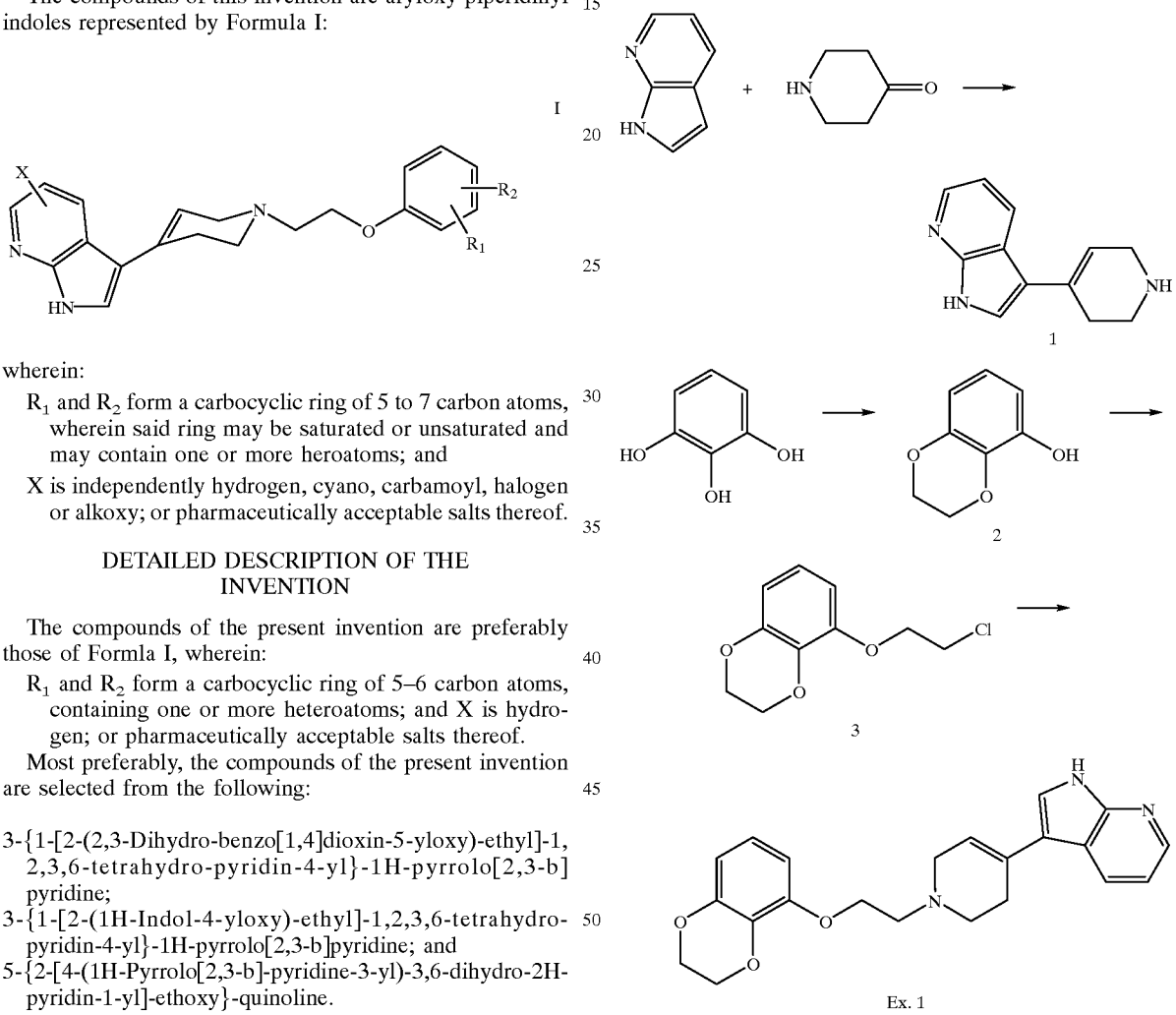

Scheme 1

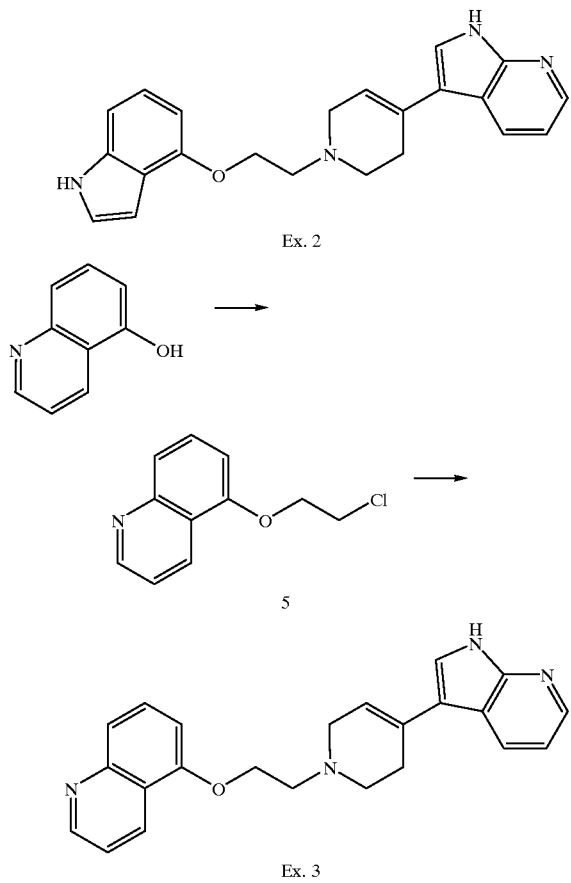

Ex. 2

Ex. 3

Specific exemplification of the production of representative compounds of this invention is provided in the following procedures.

Intermediate 1

3-(1,2,3,6-Tetrahydro-pyridin-4-yl)-1H-pyrrolo[2,3-b]pyridine 7-azindole (10 g, 85 mmol), 4-piperidone (34 g, 0.22 mol) and potassium hydroxide (16.83 g, 0.3 mol) were heated to reflux in 150 ml methanol overnight. The reaction was cooled, filtered and concentrated to give an orange slurry. The slurry was then extracted with methylene chloride and washed with water. The organic layer was dried over anhydrous magnesium, filtered and concentrated to afford 14.2 g (84%) of product as a solid: mp 195–199° C.

Intermediate 2

5-Hydroxy-(2,3)-dihydrobenzo[1,4]dioxine

Pyrogallol (5 g, 0.04 mol) was dissolved in 2-butanone (600 ml) to which potassium carbonate (1.82 g, 0.013 mol) was added. The mixture was stirred at reflux while 1,2-dibromoethane (2.48 g, 1.14 ml, 0.013 mol) was slowly added dropwise. The reaction was allowed to stir overnight and then cooled to room temperature. The mixture was poured into water (100 ml) and extracted with methylene chloride (200 ml). The organic layer was dried over anhydrous sodium sulfate, filtered, and the solvent was removed under vacuum. Chromatography (5% methanol-methylene chloride) afforded 2.74 g (45%) of product as a clear oil. MS EI m/e 152 (M$^+$)

Intermediate 3

5-(2-Chloroethoxy)-(2,3)-dihydrobenzo-[1,4]dioxane

To solution of 5-hydroxybenzodioxane (1.0 g, 6.5 mmol) and 2-chloroethanol (0.79 g, 9.9 mmol), triphenylphosphine (2.6 g, 9.9 mmol) in tetrahydrofuran (50 ml) was slowly added diisopropylazidodicarbimide (DIAD) (2.0 g, 9.8 mmol). After 2 hours, another 1.5 eq of triphenylphosphine, DIAD, and 2-chloroethanol was added and the reaction stirred for another 2 hours. The reaction mixture was poured into water (100 ml), and extracted with methylene chloride (100 ml). The organic layer was separated and dried over anhydrous magnesium sulfate, filtered, and the solvent removed under vacuum. Chromatography (20% ethyl acetate-hexanes) afforded 1.7 g (76%) of product as a white solid: mp 70.5–72.5° C.

Elemental analysis for $C_{10}H_{11}ClO_3$
Cal'd: C, 55.96; H, 5.17
Found: C, 55.57; H, 5.20

Intermediate 4

2-(1H-Indol-4-yloxy)ethylchloride

To a solution of 4-hydroxyindole (4 g, 30 mmol), 2-chloroethanol (4.83 g, 60 mmol), triphenylphosphine (15.7 g, 60 mmol) in anhydrous tetrahydroufuran (40 ml) was slowly added diisopropyl azodicarboxylate (12.1 g, 60 mmol). The reaction was allowed to stir for 2.5 hours at room temperature, then poured into methylene chloride (250 ml), washed with water (3×100 ml) and dried over anhydrous sodium sulfate, filtered and the solvent was removed under vacuum. Chromatography (20% hexanes-ethyl acetate) to remove triphenylphosphine (20% methylene chloride-hexanes) afforded 2.94 g (50%) of product as a white solid: mp 69.5–72° C.

Intermediate 5

5-(2-Chloroethoxy)-quinoline

A 100 ml three-neck oven dry flask was cooled under nitrogen. 5-Hydroxy quinoline (2 g, 14 mmol) was added as well as triphenylphosphine (5.42 g, 21 mmol) suspended in 50 ml anhydrous tetrahydrofuran. 2-Chloroethanol (1.3 ml, 21 mmol) was slowly added to above reaction mixture via syringe, followed by adding DEAD (2.98 ml, 21 mmol) via syringe. A second 1.5 eq of 2-chloroethanol, triphenylphosphine and DEAD was added. The reaction mixture was poured into 100 ml water and extracted by methylene chloride. The organic layer was dried over anhydrous sodium sulfate and concentrated. Chromatographed (20% ethyl acetate-hexanes) afforded 2.31 g (82%) of product as a solid: mp 75–78° C.

EXAMPLE 1

3-{1-[2-(2,3-Dihydro-benzo[1,4]dioxin-5-yloxy)-ethyl]-1,2,3,6-tetrahydro-pyridin-4-yl}-1H-pyrrolo[2,3-b]pyridine A solution of 5-(2-chloroethoxy)-(2,3)-dihydrobenzo [1,4]dioxane (0.5 g, 23 mmol), 3-(1,2,3,6-tetrahydro-pyridin-4-yl)-1H-pyrrolo[2,3-b]pyridine (0.56 g, 28 mmol) and triethylamine (0.65 ml, 46 mmol) in anhydrous dimethylsulfoxide (20 ml) was allowed to stir for 4 hours at 105° C. The mixture was poured into water (100 ml) and extracted with metbylene chloride (3×100 ml). The organic layer was washed with water (3×150 ml), sodium bicarbonate and dried over anhydrous sodium sulfate, filtered, and the solvent was removed under vacuum. Chromatography (10% methanol-methylene chloride) afforded 0.80 g (92%) of product as a yellow oil.

The oxalate salt was prepared in ethanol: mp 164–167° C.

Elemental analysis for $C_{22}H_{23}N_3O_3 \cdot 2C_2H_2O_4 \cdot 0.7H_2O$

Calc'd: C, 54.77; H, 5.02; N, 7.37

Found: C, 54.77; H, 4.97; N, 7.23

EXAMPLE 2

3-{1-[2-(1H-Indol-4-yloxy)-ethyl]-1,2,3,6-tetrahydro-pyridin-4-yl}-1H-pyrrolo[2,3-b]pyridine A solution of 2-(1H-indol-4-yloxy)ethylchloride (0.5 g, 26 mmol), 3-(1,2,3,6-tetrahydro-pyridin-4-yl)-1H-pyrrolo[2,3-b]pyridine (0.61 g, 31 mmol) and triethylamine (0.71 ml, 52 mmol) in anhydrous dimethylsulfoxide (20 ml) was allowed to stir for 4 hours at 80° C. The mixture was poured into water and extracted with ethyl acetate (3×100 ml). The organic layer was washed with water (3×100 ml), sodium bicarbonate and dried over anhydrous sodium sulfate, filtered, and the solvent was removed under vacuum. Chromatography (10% methanol-methylene chloride) afforded 0.95 g (97%) of product as a green oil.

The oxalate salt was prepared in ethanol: mp 106–109° C.

Elemental analysis for $C_{22}H_{22}N_4O \cdot 2C_2H_2O_4$

Calc'd: C, 57.99; H, 4.87; N, 10.40

Found: C, 57.62; H, 5.03; N, 10.36

EXAMPLE 3

5-{2-[4-(1H-Pyrrolo[2,3-b]pyridin-3-yl)-3,6-dihydro-2H-pyridin-1-yl]-ethoxy}-quinoline A solution of 5-(2-chloroethoxy)quinoline (0.5 g, 24 mmol), ), 3-(1,2,3,6-tetrahydro-pyridin-4-yl)-1H-pyrrolo[2,3-b]pyridine (0.58 g, 29 mmol) and triethylamine (0.67 ml, 48 mmol) in anhydrous dimethylsulfoxide (20 ml) was allowed to stir for 4 hours at 80° C. The mixture was poured into water dilute with sodium hydroxide solution and extracted with ethyl acetate (3×100 ml). The organic layer was washed with water (3×100 ml), sodium bicarbonate and dried over anhydrous sodium sulfate, filtered, and the solvent was removed under vacuum to give a pale yellow solid, which was triturated with ethanol-ethyl ether to afford a pale yellow solid: mp 202–205° C.

The oxalate salt was prepared in ethanol: mp 202–205° C.

Elemental analysis for $C_{23}H_{22}N_4O \cdot C_2H_2O_4 \cdot 0.5H_2O$

Calc'd: C, 72.80; H, 6.11; N, 14.77

Found: C, 72.71; H, 5.97; N, 15.37

The activity of the present compounds is demonstrated by the following standard pharmacological test procedures.

The PCR cloning of the human 5-HT$_{1A}$ receptor subtype from a human genomic library has been described previously by Chanda et al., Mol. Pharmacol., 43:516 (1993). A stable Chinese hamster ovary cell line expressing the human 5-HT$_{1A}$ receptor subtype (5-HT$_{1A}$.CHO cells) was employed throughout this study. Cells were maintained in DMEM supplemented with 10% fetal calf serum, non-essential amino acids and penicillin/ streptomycin.

Cells were grown to 95–100% confluency as a monolayer before membranes were harvested for binding studies. Cells were gently scraped from the culture plates, transferred to centrifuge tubes, and washed twice by centrifugation (2000 rpm for 10 min., 4° C.) in buffer (50 mM Tris; pH 7.5). The resulting pellets were aliquoted and maintained at −80° C. On the day of assay, the cells were thawed on ice, and resuspended in buffer. Studies were conducted using [$^3$H]8-OH-DPAT as the radioligand. The binding assay was performed in 96 well microtiter plates in a final total volume of 250 μL of buffer. Comparison experiments were performed by using 7 concentrations of unlabelled drug and a final ligand concentration of 1.5 nM. Non-specific binding was determined in the presence of 10 μM 5HT. Saturation analysis was conducted by using [$^3$H]8-OH-DPAT at concentrations ranging from 0.3–30 nM. Following a 30 minute incubation at room temperature, the reaction was terminated by the addition of ice cold buffer and rapid filtration using a M-96 Brandel Cell Harvester (Gaithersburg, MD) through a GF/B filter presoaked for 30 minutes in 0.5% polyethyleneimine.

A protocol similar to that used by Cheetham et al., Neuropharmacol., 32:737 (1993) was used to determine the affinity of compounds for the serotonin transporter. Briefly, frontal cortical membranes prepared from male Sprague-Dawley rats were incubated with $^3$H-paroxetine (0.1 nM) for 60 min at 25° C. All tubes also contained either vehicle, test compound (one to eight concentrations), or a saturating concentration of fluoxetine (10 μM) to define specific binding. All reactions were terminated by the addition of ice cold Tris buffer followed by rapid filtration using a Tom Tech filtration device to separate bound from free $^3$H-paroxetine. Bound radioactivity was quantitated using a Wallac 1205 Beta Plate® counter. Nonlinear regression analysis was used to determine IC$_{50}$ values which were converted to Ki values using the method set forth in Cheng and Prusoff, Biochem. Pharmacol., 22:3099 (1973) (Ki=IC50/((Radioligand conc.)/(1+KD))).

The [$^{35}$S]-GTPγS binding assay was similar to that used by Lazareno and Birdsall, Br. J. Pharmacol. 109:1120 (1993). Briefly, 5-HT$_{1A}$ cloned receptor membrane fragments (as used for 5-HT$_{1A}$ receptor binding assays) were stored at −70° C. When needed, membranes were rapidly thawed, centrifuged at 40,000×g for 10 minutes and resuspended at 4° C. for 10 minutes in assay buffer (25 mM HEPES, 3 mM MgCl$_2$, 100 mM NaCl, 1 mM EDTA, 10 uM GDP, 500 mM DTT, pH 8.0). These membranes were then incubated for 30 min at 30° C. with [$^{35}$S]GTPgS (1 nM) in the presence of vehicle, test compound (one to eight concentrations), or excess 8-OH-DPAT to define maximum agonist response. All reactions were terminated by the addition of ice cold Tris buffer followed by rapid filtration using a Tom Tech® filtration device to separate bound from free [$^{35}$S]GTPgS. Agonists produced an increase in the amount of [$^{35}$S]GTPgS bound whereas antagonists produced no increase in binding. Bound radioactivity was counted and analyzed as above.

The following assays were performed by incubating the cells with DMEM containing 25 mM HEPES, 5 mM theophylline and 10 μM pargyline for a period of 20 minutes at 37° C. Functional activity was assessed by treating the cells with forskolin (1 uM final concentration) followed immediately by test compound (6 concentrations) for an additional 10 min at 37° C. In separate experiments, 6 concentrations of antagonist were preincubated for 20 min prior to the addition of 10 nM 8-OH-DPAT and forskolin. The reaction was terminated by removal of the media and addition of 0.5 ml ice cold assay buffer. Plates were stored at −20° C. prior to assessment of cAMP formation by a cAMP SPA assay (Amersham).

| Example No. | 5-HT$_{1A}$ (Ki, nM) | ST (K$_i$, nM,) | GTPγS ED50 (% Emax) | cAMP ED50 (Emax) |
|---|---|---|---|---|
| 1 | 43.9 | 18.0 | (30%) | |
| 2 | 10.9 | 1.46 | 38.9 (9.0%) | 12.4 (0%) |
| 3 | 71.6 | 6.89 | 181 (0%) | 90.1 (0%) |

As demonstrated by the results set forth above, the compounds of the present invention are active towards 5HT1A receptors and generally elevate serotonin levels by inhibiting 5-HT transport. Accordingly, the present compounds should be useful in treating disorders related to defects in serotonin concentration.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Any of the solid carriers known to those skilled in the art may be used with the compounds of this invention. Particularly suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidone, low melting waxes and ion exchange resins.

Liquid carriers may be used in preparing solutions, suspensions, emulsions, syrups and elixirs of the compounds of this invention. The compounds of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) and their derivatives and oils (e.g., fractionated coconut oil and arachis oil). For parenteral administration, the carrier can also be an oily ester such as ethyl oleate and isopropyl myristate. Sterile liquid carriers are used in compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Compositions for oral administration may be either liquid or solid composition form.

Preferably, the pharmaceutical compositions containing the compounds of this invention are in unit dosage form, e.g., tablets or capsules. In such form, the compositions may be sub-divided in unit doses containing appropriate quantities of the present compounds. The unit dosage forms can be packaged compositions, for example, packeted powders, vials, ampoules, prefilled syringes or sachets containing liquids. Alternatively, the unit dosage form can be, for example, a capsule or tablet itself, or it can be the appropriate number of any such compositions in package form.

The therapeutically effective amount of the compounds of this invention that is administered and the dosage regimen depends on a variety of factors, including the weight, age, sex, and medical condition of the subject, the severity of the disease, the route and frequency of administration, and the specific compound employed, and thus may vary widely. However, it is believed that the pharmaceutical compositions may contain the compounds of this invention in the range of about 0.1 to about 2000 mg, preferably in the range of about 0.5 to about 500 mg and more preferably between about 1 and about 100 mg. Projected daily dosages of active compound are about 0.01 to about 100 mg/kg body weight. The daily dose can be conveniently administered two to four times per day.

The present invention may be embodied in other specific forms without departing from the spirit and essential attributes thereof and accordingly, reference should be made to the appended claims, rather than to the foregoing specification, as indicating the scope of the invention.

What is claimed is:

1. A compound of the formula:

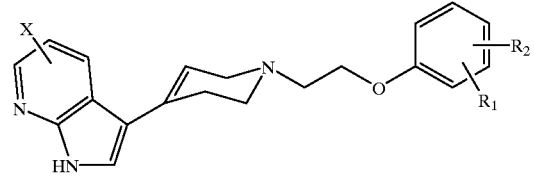

wherein:

$R_1$ and $R_2$ form a carbocyclic ring of 5 to 7 carbon atoms, wherein said ring may be saturated or unsaturated and may contain one or more heteroatoms; and X is independently hydrogen, cyano, carbamoyl, halogen or alkoxy; or pharmaceutically acceptable salts thereof.

2. A compound as in claim 1 wherein:

$R_1$ and $R_2$ form a carbocyclic ring of 5–6 carbon atoms, containing one or more heteroatoms; and X is hydrogen; or pharmaceutically acceptable salts thereof.

3. The compound of claim 1 which is 3-{1-[2-(2,3-Dihydro-benzo[1,4]dioxin-5-yloxy)-ethyl]-1,2,3,6-tetrahydro-pyridin-4-yl}-1H-pyrrolo[2,3-b]pyridine.

4. The compound of claim 1 which is 3-{1-[2-(1H-Indol-4-yloxy)-ethyl]-1,2,3,6-tetrahydro-pyridin-4-yl}-1H-pyrrolo[2,3-b]pyridine.

5. The compound of claim 1 which is 5-{2-[4-(1H-Pyrrolo[2,3-b]-pyridine-3-yl)-3,6-dihydro-2H-pyridin-1-yl]-ethoxy}-quinoline.

6. A pharmaceutical composition comprising a compound of the formula:

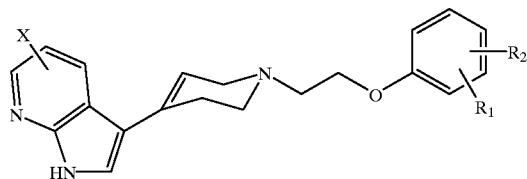

wherein:

R₁ and R₂ form a carbocyclic ring of 5 to 7 carbon atoms, wherein said ring may be saturated or unsaturated and may contain one or more heteroatoms; and X is independently hydrogen, cyano, carbamoyl, halogen or alkoxy; or pharmaceutically acceptable salts thereof.

7. A method for treating depression in a patient in need thereof comprising administering to said patient an antidepressant effective amount of a compound of the formula:

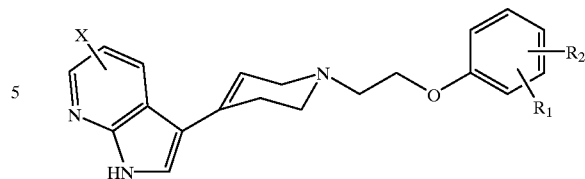

wherein:

R₁ and R₂ form a carbocyclic ring of 5 to 7 carbon atoms, wherein said ring may be saturated or unsaturated and may contain one or more heteroatoms; and X is independently hydrogen, cyano, carbamoyl, halogen or alkoxy; or pharmaceutically acceptable salts thereof.

* * * * *